(12) United States Patent
Bauer et al.

(10) Patent No.: US 10,004,444 B2
(45) Date of Patent: Jun. 26, 2018

(54) COLLECTION ASSEMBLY, IN PARTICULAR FOR BLOOD SAMPLES

(71) Applicant: Greiner Bio-One GmbH, Kremsmuenster (AT)

(72) Inventors: Christian Bauer, Kremsmuenster (AT); Georg Kofler, Inzersdorf (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 146 days.

(21) Appl. No.: 15/028,058

(22) PCT Filed: Oct. 9, 2014

(86) PCT No.: PCT/AT2014/050237
§ 371 (c)(1),
(2) Date: Jun. 10, 2016

(87) PCT Pub. No.: WO2015/051389
PCT Pub. Date: Apr. 16, 2015

(65) Prior Publication Data
US 2016/0278680 A1 Sep. 29, 2016

(30) Foreign Application Priority Data

Oct. 11, 2013 (AT) .............................. A 50658/2013

(51) Int. Cl.
*A61B 5/15* (2006.01)
*B01L 3/00* (2006.01)

(52) U.S. Cl.
CPC .. *A61B 5/150343* (2013.01); *A61B 5/150022* (2013.01); *A61B 5/150351* (2013.01);
(Continued)

(58) Field of Classification Search
None
See application file for complete search history.

(56) References Cited

U.S. PATENT DOCUMENTS

| 4,092,113 A | 5/1978 | Hardy |
| 4,576,185 A | 3/1986 | Proud et al. |

(Continued)

FOREIGN PATENT DOCUMENTS

| DE | 103 40 538 A1 | 4/2005 |
| EP | 0 146 074 A1 | 6/1985 |

(Continued)

OTHER PUBLICATIONS

Response to the European Patent Office in PCT/AT2014/050237, dated Jun. 25, 2015, with English translation of relevant parts.
(Continued)

*Primary Examiner* — Jill Alice Warden
*Assistant Examiner* — Julie L Tavares
(74) *Attorney, Agent, or Firm* — Collard & Roe, P.C.

(57) ABSTRACT

The application relates to a collection assembly (1), in particular for blood samples, comprising a sample container (2) and a closure device (3) which has a closure cap (22) and a pierceable septum (26) held on the closure cap. At its open end (4) delimited by an end face (11), the sample container has a flange (13) and an annular skirt (15), the flange projecting radially beyond a side wall (7). The annular skirt (15) extends axially from a flange end (14) to a closed end (5) of the sample container (2). The sample container (2), the flange (13) and the annular skirt form a one-piece component. Between an outer surface (9) of the side wall (7) and an inner annular skirt surface (16) facing toward this outer surface, there is an approximately tubular free space (17) which is delimited in the axial direction in the region of the open end (4) by the flange (13).

10 Claims, 4 Drawing Sheets

(52) U.S. Cl.
CPC ......... *B01L 3/5021* (2013.01); *B01L 3/50825* (2013.01); *B01L 2200/023* (2013.01); *B01L 2200/025* (2013.01); *B01L 2200/026* (2013.01)

(56) References Cited

U.S. PATENT DOCUMENTS

| | | |
|---|---|---|
| 4,687,479 A | 8/1987 | Sarstedt et al. |
| 5,246,434 A | 9/1993 | Ebara |
| 5,288,466 A | 2/1994 | Burns |
| 5,384,096 A | 1/1995 | Burns |
| 6,562,300 B2 | 5/2003 | Rosen et al. |
| 8,448,800 B2 | 5/2013 | Konrad |
| 2012/0141341 A1 | 6/2012 | Bartfeld et al. |

FOREIGN PATENT DOCUMENTS

| | | |
|---|---|---|
| EP | 0 182 370 A2 | 5/1986 |
| EP | 0 510 683 A1 | 10/1992 |
| EP | 1 066 882 B1 | 1/2001 |
| EP | 1 711 412 B1 | 11/2010 |

OTHER PUBLICATIONS

International Search Report of PCT/AT2014/050237, dated Jan. 30, 2015.

Fig.1

COLLECTION ASSEMBLY, IN PARTICULAR FOR BLOOD SAMPLES

CROSS REFERENCE TO RELATED APPLICATIONS

This application is the National Stage of PCT/AT2014/050237 filed on Oct. 9, 2014, which claims priority under 35 U.S.C. § 119 of Austrian Application No. A 50658/2013 filed on Oct. 11, 2013, the disclosure of which is incorporated by reference. The international application under PCT article 21(2) was not published in English.

The invention relates to a collection assembly, in particular for blood samples.

U.S. Pat. No. 4,092,113 A describes a collection assembly for blood samples comprising a sample container, a closure device closing the latter and a support tube receiving the sample container. The sample container has an open end, an end closed by a base and a side wall extending between the two ends with an outer face and an inner face. The side wall and the base define a collecting space for the blood sample. The sample container also comprises at its open end delimited by an end face a flange projecting radially over the side wall and an annular skirt. The annular skirt is arranged on an end of the flange facing away from the side wall and extends in axial direction from the flange end to the closed end. The sample container, the flange and the annular skirt together form a one-piece component. Between the outer face of the side wall and an inner annular skirt face of the annular skirt facing the side wall an approximately tubular free space is formed for receiving the support tube. A cap casing of the closure cap grips externally over the sample container. A tubular edge projects in axial direction from the flange in the direction facing away from the closed end and is provided with an external thread. On the inner face of the cap casing an internal thread is arranged. In the closure cap in the region of its end wall a pierceable, disc-like sealing element is arranged, on which the tubular edge rising up from the flange bears in the closed position.

A similarly designed removal assembly for blood samples is known from US 2012/0141341 A1. The removal assembly comprises a sample container which is inserted into a support tube and is closed by means of a closure device. The sample container comprises a flange-like edge which bears on an end wall of the open end of the support tube. Furthermore, in the region of the open end between the sample container and the support tube a locking device is arranged in order to obtain a mutual fixing and mounting of the sample container in the support tube. The cap casing of the closure device grips over the open end of the support tube and is held locked thereon in the region of its outer wall.

From EP 1 066 882 B1 a generic arrangement is known for collecting blood samples, comprising a sample container, which has an open end, an end closed by a base and a side wall extending between the open end and the closed end with an outer surface and an inner surface. The side wall is delimited in the region of the open end by an end face, wherein the side wall and the base define a collecting space. The sample container can be closed by a closure device and comprises a closure cap and a pierceable septum held on the closure cap. The closure device in the closed position closes the collecting space of the sample container in the region of its open end. The outer cap casing of the closure cap grips externally over the open end of the sample container on the outside and is supported on a support ring spaced apart from the open end. The inner cap casing projects into the collecting space and bears with a radially projecting ring base on the inner surface of the side wall of the sample container. A pierceable septum is arranged on the open end face of the inner cap casing facing the base.

From EP 1 066 882 B1 a generic arrangement is known for collecting blood samples, comprising a sample container, which has an open end, an end closed by a base and a side wall extending between the open end and the closed end with an outer surface and an inner surface. The side wall is delimited in the region of the open end by an end face, wherein the side wall and the base define a collecting space. The sample container can be closed by a closure device and comprises a closure cap and a penetrable septum held on the closure cap. The closure device in the closed position closes the collecting space of the sample container in the region of its open end. The outer cap casing of the closure cap grips externally over the open end of the sample container on the outside and is supported on a support ring spaced apart from the open end. The inner cap casing projects into the collecting space and bears with a radially projecting ring base on the inner surface of the side wall of the sample container. A penetrable septum is arranged on the open end face of the inner cap casing facing the base.

Further similarly designed arrangements for collecting blood samples are also known from U.S. Pat. No. 5,288,466 A and U.S. Pat. No. 5,384,096 A.

The disadvantage of all of these sample collecting arrangements is that the latter were not easy to handle in all applications and the centrifugation of the collected body fluid was only possible with the aid of additional components. This was the case because such sample collecting assemblies have smaller dimensions than standardized blood sample collecting tubes.

The underlying objective of the present invention is to create a collection assembly for collecting capillary blood in particular, which can be applied universally by the user.

Said objective is achieved by the features disclosed herein.

The advantage resulting from the features according to the invention is that in this way a double-walled cap is formed in which the tubular or annular free space formed between the outer cap casing and the inner cap casing is used for receiving the mostly lip-shaped mounting edge of the sample container. Furthermore, by means of the inner cap casing a defined access opening is created from the closure cap up to the collecting space. Furthermore, the outer cap casing can be designed such that the latter can be provided for the simpler operation and handling of the closure device with suitable aids. Furthermore, in the transitional area between the flange and the annular skirt the adequate support of the closure device on the sample container can be ensured. In this way however also in cooperation with the annular skirt the outer dimensional shape of standard closure caps can be formed, as used in blood sample tubes.

Furthermore, an unintentional loosening of the closure device from the sample container can be prevented up to the point of exceeding a predefined releasing force. In this way however, also with a closure device located in the closed position the unintentional loosening of the closure device, caused by for example light knocks caused by the filled collection assembly falling over, can be prevented. By having the approximately same configuration of external dimensions in this way a connected structural unit can be created in which with a fitted closure device in cooperation with the annular skirt a dimensionally continuous structural unit can be created. If in addition in the region of the open end face of the annular skirt, which faces the base, on the outside over the circumference at least partly a flange projecting in radial direction over the annular skirt is arranged, in this way a direct bearing of the outer cap casing of the closure cap on a bearing surface can be avoided in a lying position of the latter. Thus also in a lying position of the collection assembly the unintentional loosening of the closure device from the sample container can be prevented.

By arranging the septum spaced apart from the end wall in this way with a fitted closure device access to the collecting space is interrupted. Furthermore, in this way a unit is created which can be removed jointly from the sample container and then can be fitted back on for the closure thereof.

By providing an additional annular skirt, which is connected by a flange projecting radially over the side wall of the sample container to the latter, on the sample container a cap-like component is provided directly, by means of which multiple, more universal applications are possible. Thus on first use after collecting the body fluid, in particular the capillary blood, the collection assembly can be used without the aid of additional components in a standardized centrifuge device. By providing the flange in connection with the annular skirt in this way a perfect transfer of force can be performed directly to the respective centrifuge along with the support of the collection assembly. Furthermore, it is also possible in this way to ensure the sufficient support and if necessary holding of the closure device on the sample container. With a fitted closure device on the sample container thus in cooperation with the annular skirt a cap-like form can be created, as is usual in medical technology for the standardized cap dimensions of blood sample collecting tubes.

A further possible application is provided by using the tubular free space formed between the inner annular skirt surface of the annular skirt and the outer surface of the side wall to insert the sample container into a standardized blood sample removal tube or support tube, to enable in this way the mounting of the sample container on said tube. In this way a more universal application of the sample container is created which can be supplied alone or in combination with an additional support tube for centrifugation. Furthermore, however also a more simple and inexpensive production process is made possible as no additional parts have to be made to create a functioning collection assembly.

A further embodiment in which a first thread arrangement is arranged or formed on the inner annular skirt surface is also advantageous as in this way it is possible to screw the sample container over the annular skirt arranged thereon with an additional thread arrangement provided on a support tube. In this way an even more secure mutual connection can be created compared to an insertion or clamping connection.

A configuration in which the sample container includes a receiving edge connected to the side wall, and the end face of the open end projects in axial direction in the direction facing away from the base is also advantageous as in this way the filling process is made possible without additional components in the designated collection or collecting chamber of the sample container. In this way for the filling process only the closure device needs to be removed and the filling process can be performed directly afterwards. By omitting additional components in this way the manufacturing and material costs of the collection assembly can be reduced.

By means of another configuration in which the receiving edge extends over only a portion of the periphery of the side wall and a receiving edge surface facing the collecting space passes in axial direction in an approximately straight line into the inner surface formed by the side wall it is possible to perform a perfect filling process. In this way not only can sufficient visual contact with the collection site can be ensured but also the unhindered inflow of the body fluid, in particular capillary blood, collected in the collecting space is possible.

According to another embodiment variant in which the sample container at its closed end has a tubular edge projecting over the closed end in axial direction in the direction facing away from the open end it is possible for the sample container to be placed directly on the tubular edge on a defined base or positioning surface. This is performed if the tubular edge on its side facing away from the base ends in a plane aligned perpendicular to the longitudinal axis.

By means of a development the septum forms on its outer circumferential side with the inner surface of the side wall in the closure position a continuous, complete enclosure of the collecting space. In this way it is possible to reliably prevent the entry of dirt up to the removal of the closure device and also ensure the sterility until the first time of opening.

A configuration is also advantageous in which between the open face end of the outer cap casing and the flange or the annular skirt a centering arrangement is provided with first and second centering elements working together in the closed position as in this way an even more exact mutual alignment of the closure device can be achieved, in particular of the closure cap, relative to the sample container and the annular skirt arranged thereon.

According to an advantageous development that includes a support tube it is thus possible to also feed the collection assembly to an automated analysis process with standardized analysis devices and perform the investigations there. This is because in such automated analysis methods standardized dimensions are necessary with regard to length, cross-sectional form and diameter or external dimensions. By inserting the sample container into the support tube, a collection assembly can be provided which corresponds to the standardized dimensions of blood sample removal tubes. Furthermore, in this way also the sample container, in particular its side wall, can be designed to have a dimension which is suitable for being inserted or received inside the support tube. In this way however even with a constant filling volume compared to a previously used sample containers due to the increase of the external dimension a shorter distance of the base from the open end can be achieved than was the case in previously conventional removal devices.

A configuration in which the support tube is provided on an outer surface of its open first end section with a second thread arrangement is also advantageous as in this way a connected collection assembly can be provided which also has a stable connection when in use. In this way it is possible to connect the sample container without additional components to a standardized blood sample tube and thus perform the previously described automated analyses or investigations of the sample content.

Lastly, another configuration is also possible in which an anti-rotation device is included between the annular skirt and the support tube, as in this way separation is made difficult and can be completely prevented. This is used if a confusion of the samples is possible, if for example if an information carrier is arranged or applied only on the support tube. In this way the sample held the sample container is always clearly assigned to a patient. Thus it is not necessary to mark the sample container directly. As the dimensions of the sample containers are designed to be smaller relative to the support tube more space is available for attaching the information carrier onto the support tube. In this way standardized information carriers can be used.

For a better understanding of the invention the latter is explained in more detail with reference to the following Figures.

In a much simplified, schematic representation.

First of all, it should be noted that in the variously described exemplary embodiments the same parts have been given the same reference numerals and the same component names, whereby the disclosures contained throughout the entire description can be applied to the same parts with the same reference numerals and same component names. Also details relating to position used in the description, such as e.g. top, bottom, side etc. relate to the currently described and represented figure and in case of a change in position should be adjusted to the new position.

FIG. 1 to 4 show a collection assembly 1 in different configurations, which is used in particular for removing body fluids, such as blood samples. The collection assembly 1 shown here has a smaller external dimension and a smaller receiving volume than the usually used blood sample removal tubes with mostly standardized dimensions. Said collection assembly 1 is preferably used for the removal of capillary blood, which is only taken in smaller volumes, is and stored for subsequent investigations in the collection assembly 1.

The collection assembly 1 shown here comprises a sample container 2 and a closure device 3.

The sample container 2 comprises in turn an open end 4 and a closed end 5. The closed end 5 can thus be designed to be closed by a base 6. A side wall 7 extends between the open end 4 and the closed end 5. Furthermore, a longitudinal axis 8 extends between the open end 4 and the closed end 5, which can also preferably be denoted as a central longitudinal axis. The cross-sectional form of the sample container 2 can be selected to be different, wherein however mostly a circular round cross-section is selected as the preferred cross-sectional form. In order to enable the demolding of the sample container 2 produced, preferably in an injection molding process, corresponding mold inclines need to be provided, as is usual in such components. Preferably, also a plastic material is selected as the material for the sample container. In this case the material can be designed to be mostly transparent to crystal clear and can be selected from a group consisting of FP (polypropylene), PS (polystyrene), PET (polyethylene terephthalate), PE (polyethylene), PA (polyamide) or PC (polycarbonate).

The side wall 7 of the sample container 2 also comprises an outer surface 9 and an inner surface 10 spaced apart therefrom in a wall thickness of the side wall 7. The side wall 7 is also delimited in the region of the open ends 4 by an end face 11. The side wall 7 with its inner surface 10 defines together with the base 6 a collecting space 12, which is used for taking the body fluid to be taken or filled, in particular blood, particularly preferably capillary blood. The sample container 2 also comprises on its open end 4 delimiting the end face 11 a flange 13 projecting over the side wall 7 in radial direction relative to the longitudinal axis 8. The flange 13 comprises on its side facing away from the side wall 7 or longitudinal axis 8 an outer flange end 14.

On said flange end 14 facing away from the side wall 7 also an annular skirt 15 is arranged or formed, wherein the annular skirt 15 extends from the flange end 14 in axial direction to the base or the closed end 5 of the sample container 2. The annular skirt 15 comprises an inner annular skirt surface 16 facing towards the side wall 7 or its outer surface 9. Furthermore, between the outer surface 9 and the side wall 7 and the inner annular skirt surface 16 of the annular skirt 15 facing towards the side wall 7 an approximately tubular free space 17 is formed. The said free space 17 running over the circumference extends in axial direction from the end of the annular skirt 15 facing away from the flange 13 up to the flange 13. In this way in axial direction the free space 17 is closed or delimited in the region of the open end 4 by the flange 13.

The sample container 2, the flange 13 and the annular skirt 15 preferably form a one-piece component which is mostly produced in an injection molding process in an injection molding die in a known manner.

The function of the flange 13 with the annular skirt 15 arranged spaced apart from the outer surface 9 of the side wall 7 is explained in more detail in one of the following Figures.

In a possible development on the inner annular skirt surface 16 of the annular skirt 15 a first thread arrangement 18 is arranged or formed. It should be mentioned that the thread arrangement can be defined as a single or multiple thread and also a plurality of threads or thread segments. Thus it would be possible, for example, to design the first thread arrangement 18 as described in EP 1 711 412 B1 with the same applicant for the cap described there for closing the receiving container.

It would thus be possible to use the method described in EP 1 711 412 B1 for assembling the collection assembly 1 described here. More detailed explanations about this are found in the description of FIGS. 3 and 4.

To facilitate the filling of the sample, in particular blood, into the collecting space 12 of the sample container 2, an in particular lip-shaped receiving edge 19 can be provided. The receiving edge 19 is preferably arranged on the end face 11 and connected in one piece with the side wall 7. The latter also projects over the ends face 11 of the open end 4 in axial direction to the direction facing away from the base 6. In this way it is possible that the receiving edge 19 only extends over a portion of the circumference of the side wall 7. A receiving edge surface 20 facing towards the collecting space 12 passes in axial direction approximately linearly, in particular in a plane, into the inner surface 10 formed by the side wall 7. In this way a planar transition and simple filling is possible without an additional interfering retaining edge.

Furthermore, the sample container 2 can have on its closed end 5 a tubular edge 21 which projects over the end 5 closed by the base 6 in axial direction in the direction facing away from the open end 4. Mostly the edge 21 ends on its side facing away from the open end 4 in a plane aligned perpendicular to the longitudinal axis 8. Said plane forms for example a standing surface for the collection assembly 1, in order to place the latter on a standing surface not shown in more detail, such as for example a laboratory bench or the like in perpendicular direction. By means of the planar configuration of the edge 21 also a certain spacing of the base 6 from the edge end, which is also designed to be open, is achieved, whereby as a function of the overhang of the edge 21 in axial direction over the base 6, the total length of the sample container 2 can be determined. In this way if is also possible, for example at the same component length of the sample container 2 to arrange the base 6 at a predefined distance from the end face 11 on the inside of the side wall 7, in order to adjust or adapt the holding volume to the respectively desired incidence of use.

The closure device 3 comprises in turn a closure cap 22 with an outer cap casing 23, an inner cap casing 24 arranged spaced apart in radial direction relative to the longitudinal axis 8 and an end wall 25 connecting the two cap casings 23, 24 in radial direction. Preferably, the two cap casings 23, 24 are aligned concentrically to one another relative to the longitudinal axis 8. The connection of the two cap casings 23, 24 in radial direction through the end wall 25 is performed with a closure cap 22 fitted onto the open end 4 of the sample container 2 on the side of the closure 22 facing away from the open end 4. The inner cap casing 24 forms a through opening to thus enable access into the collecting space 12 even with a fitted closure device 3.

The closure device 3 also comprises in this example embodiment in addition to the closure cap 22 a penetrable septum 26 held on the closure cap 22. The septum 26 is used with a fitted closure device 3 to seal the collecting space 12 from the outer environment. In this way the penetrable septum 26 can also be made from an self-resealing material. The material can be selected from a group including bromobutyl rubber, TPE, natural or synthetic rubber. TPE can be used as the preferred material, as the latter can also be processed in an injection molding process. The septum 26 is designed so that the latter in the closed position of the closure device 3 forms a fluid and/or gas-tight closure of the collecting space 12 in the region of the open end 4.

In this example embodiment the septum 26 is arranged or formed on an open face end 27 of the inner cap casing 24 arranged to be spaced apart from the end wall 25. Furthermore, the septum 26 has a radially circumferential sealing surface 28. In the closed position the septum 26 is inserted into the open end 4 of the sample container 2 so that the sealing surface 28 in the closed position bears on the inner surface 10 of the side wall 7. This application is performed in particular in a sealing manner. In this way the collecting space 12 or collecting space can also be sealed in the region of the open end 4 by a fitted closure device 3. Furthermore, the septum 26 extends over the full surface over the whole open end 4 of the sample container 2 in the region of its inner surface 10. The septum 26 is designed in the present embodiment as a disc-like component and is connected to the inner cap casing 24 or arranged on the latter. By selecting a different material for the closure cap 22 and the septum 26 the connection can be performed by adhesion, welding or other thermal or connecting processes. Independently of this however it would also be possible on selecting different materials to produce the closure device 3 in a co-injection molding process. A further option would however also be to make the whole closure device 3 comprising the closure cap 22 and the septum 26 from the same material.

The outer cap casing 23 also comprises an open face end 29 on its side opposite the end wall 25. With a closure device 3 located in the closed position the open face end 29 of the outer cap casing 23 bears on the flange 13 or the annular skirt 15. This is mostly performed in the corner or transitional area between the previously described components.

Figure 2:
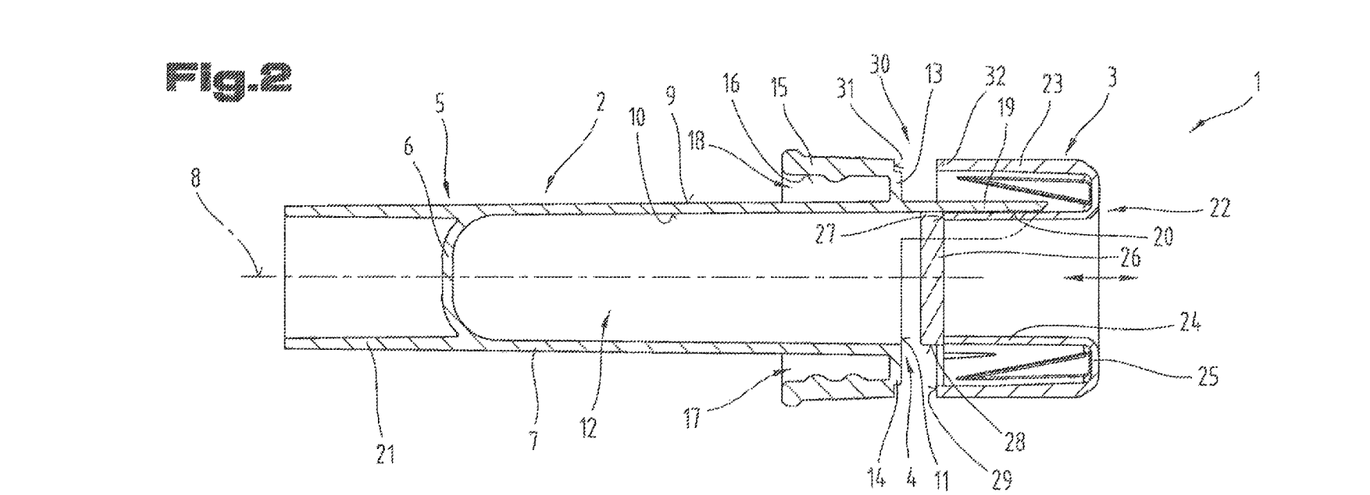
FIG. 2 shows the sample container with a partly removed closure device according to FIG. 1, in axial cross-section.
Figure 3:
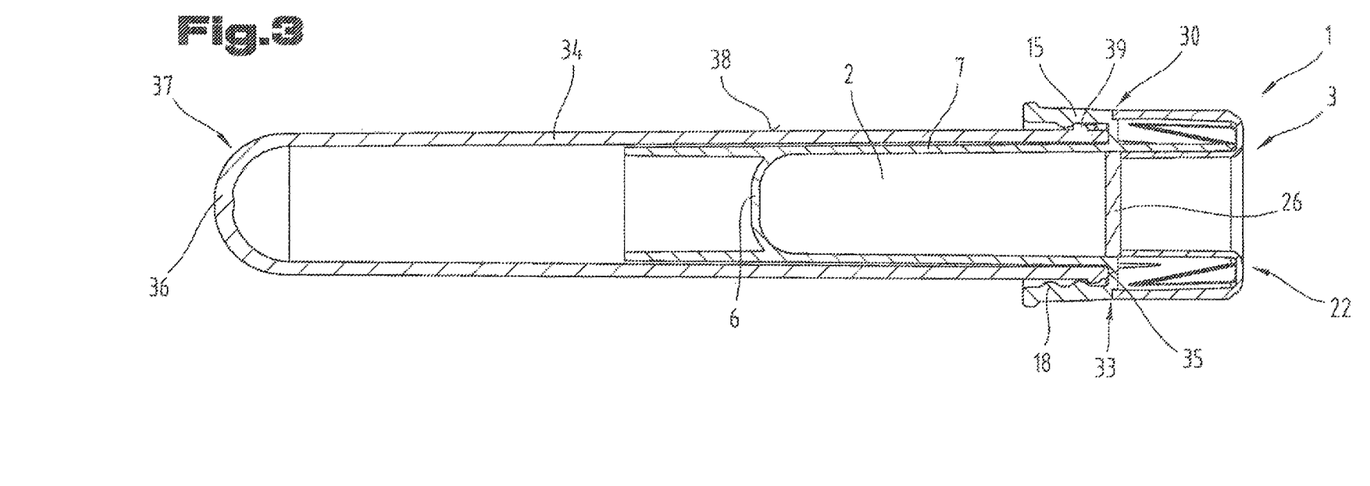
FIG. 3 shows the sample container with a closure device according to FIGS. 1 and 2, which is inserted into an additional support tube, in axial cross-section.

As shown more clearly from an overview of FIGS. 2 and 3, between the open face end 29 of the outer cap casing 23 and the flange 13 or the annular skirt 15 a centering arrangement 30 can be provided. The centering arrangement 30 comprises cooperating first and second centering elements 31, 32 which work together accordingly in the closed position. Thus in this embodiment the first centering element 31 is designed as an outwardly open centering groove which is arranged or formed in the flange 13 or the annular skirt 15 in the transitional area. Preferably, the first centering element 31 is designed to be continuous over the whole circumference of the flange 13 or the annular skirt 15.

The second centering element 32 forms the open face end 29 of the outer cap casing 23. Furthermore, it is also shown here that the outer cap casing 23 projects over the inner cap casing 24 in axial direction. This dimension can correspond to the depth or the length of the first centering element 31 extending in axial direction.

In addition to this it would also be possible however to form or provide a holding device 33 between the open face end 29 of the outer cap casing 23 and the flange 13 or the annular skirt 15. For a better overview the holding device 33 is not shown, whereby the holding device 33 can comprise cooperating first and second holding elements. In this way in addition to centering the closure cap 22 or the whole closure device 3 a specific holding or locking can be provided between the closure device 3 and the sample container 2, in particular its open end 4, in the transitional area between the flange 13 and the annular skirt 15.

Preferably, the flange 13 or the annular skirt 15 has an outer cross-sectional form or external dimension, which corresponds approximately to an outer cross-sectional form of an outer external dimension of the outer cap casing 23. In this way projecting edges can be avoided in the transitional area between the annular skirt 15 or the flange end 14 of the flange 13 and the outer cap casing 23. Furthermore, however also an optically connected structural unit is created. On the annular skirt 15 in the region of its open end face on its outer surface a beading can be provided projecting radially preferably continuously over the circumference. Said beading is used in the assembled state in a lying arrangement of the collection assembly 1 to avoid the direct placing of the closure device 3, in particular its closure cap 22 onto a not shown bearing surface. If the beading is only formed in some section and/or with a different radial projection over the outer surface of the annular skirt viewed over the circumference, a rolling movement of the collection assembly 1 can be prevented.

The dimension of the inner cap casing 24 as viewed in radial direction is preferably selected so that the latter corresponds approximately to the inner cross-sectional dimension of the inner surface 10 of the side wall 7. Preferably, the external dimension is selected to be slightly smaller than the latter. The septum 26 preferably projects over the inner cap casing 24 in radial direction. In order to achieve a suitable pre-centering between the septum 26 and the inner cap casing 24 it would still also be possible hereto provide a suitably designed centering arrangement, for example in the form of a peripheral annular groove. Furthermore, it would also be possible here to provide only individual holding elements on the inner cap casing 24 in order in this way to also achieve a mechanical holding of the septum 26 on the closure cap 22, in particular its inner cap casing 24.

Figure 4:
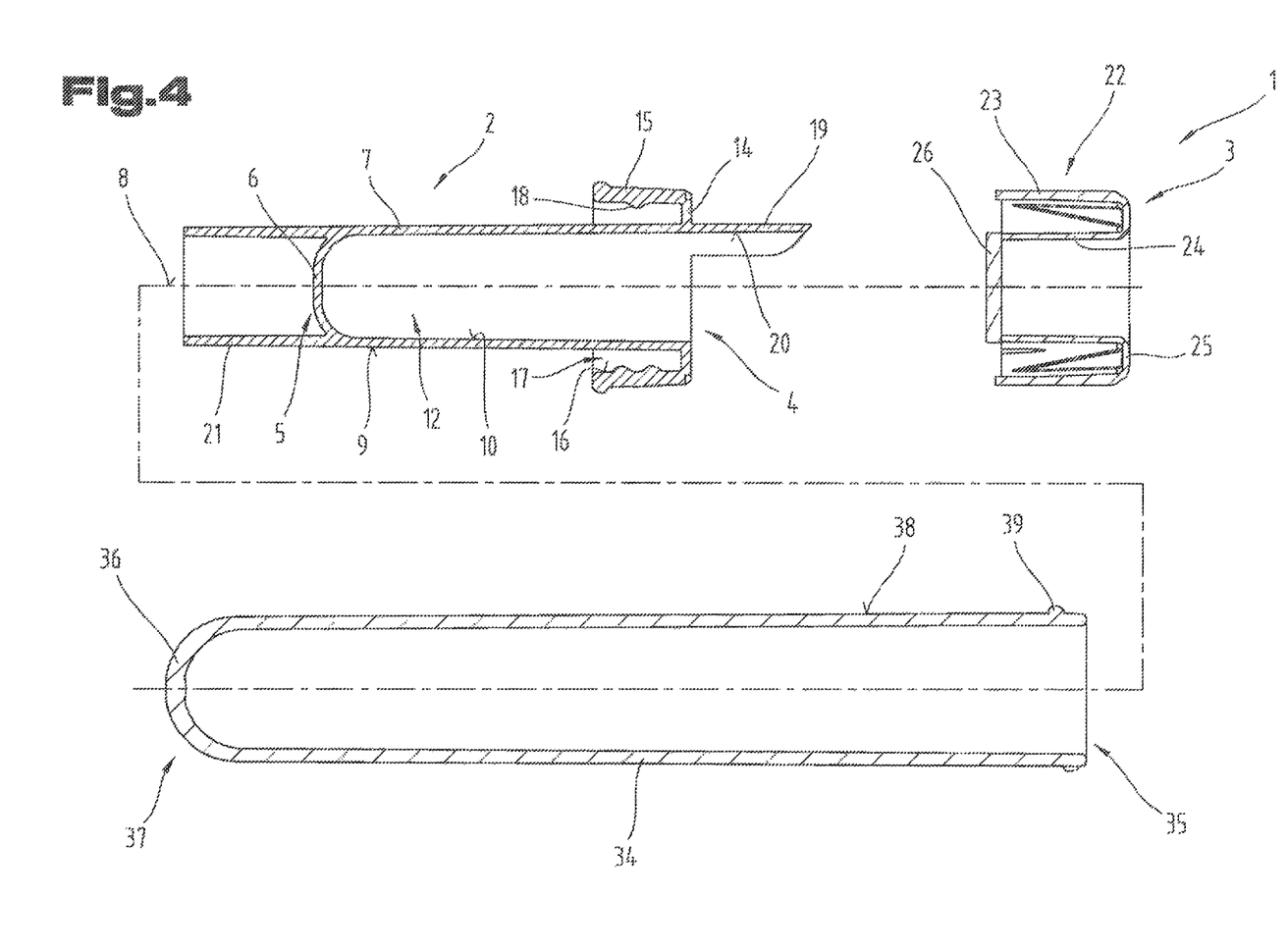
FIG. 4 shows the collection assembly according to FIG. 1 to 3, in axial cross-section and with a separated position of the individual components.

As shown better in FIGS. 3 and 4, the collection assembly 1 can also comprise an additional support tube 34. The dimensions of the support tube 34 can correspond to the standard dimensions commonly used for blood sample collecting tubes. Thus for example the diameter can be 13 mm or 16 mm, whereby the latter can have a structural length of for example 70 mm or 100 mm.

The support tube 34 comprises an open first end section 35 and a second end section 37 preferably closed by a support tube base 36. The previously described sample container 2 can be inserted with its side wall 7 and if necessary the edge 21 arranged thereon into the inner chamber of the support tube 34, wherein the open first end section 35 of the support tube 34 projects into the tubular tree space 17 formed between the outer surface 9 of the side wall 7 and the annular skirt 15. In this case the flange 13 can be used as a stop or delimitation for the insertion movement of the two components towards one another. When fully inserted the end face of the support tube 34 can be moved to bear on the flange 13 and be supported on the latter.

Preferably, the support tube 34 comprises in the region of its open end section 35 and on its outer surface 38 a second thread arrangement 39 or the latter is provided therewith. In this way it is possible for the user of the sample container 2 to use the latter for forming the collection assembly 1, for example for the centrifugation of the blood filled into the collecting space 12 or collecting chamber, in a standardized centrifuge.

FIG. 4 shows the individual parts for forming the whole collection assembly 1 in a separated position in an exploded view generally used in the art. For the formation of the closure device 3 the closure cap 22 needs to be provided or designed with the septum 26. In order to be able to provide a sterile inner chamber or collecting space 12 for the delivery, the closure device 3 needs to be fitted onto the open end 4 so that on the one hand the sealing surface 28 of the septum 26 is fitted to bear against the inner surface 10 of the side wall 7. The outer cap casing 23 of the closure cap 22 can be supported on the outer transitional area between the flange 13, in particular its flange end 14, and the annular skirt 15. Additional centering can also be provided by means of the centering arrangement 30.

To perform the process of collecting and filling blood into the collecting space 12 the closure device 3 needs to be removed and then the filling process is performed possibly with the assistance of the receiving edge 19. If a sufficient amount has been filled into the collecting space 12 the open end 4 is closed again by the closure device 3.

Thus it is possible to subject the sample container 2 with the sample contained therein directly to centrifugation or other evaluation processes and analyses. In this case the support or bearing of the sample container 2 can be on the face end or the end face of the annular skirt 15 facing the base 6.

If this sort of support or bearing of the annular skirt 15 on the centrifuge, which is not shown in more detail here, is not possible the sample container 2 can be inserted into the support tube 34 in its closed state by the closure device 3, as already described above. A mutual fixing or mounting of the sample container 2 can thus be performed via the cooperating first and second thread arrangements 18 or 39.

As already mentioned briefly above, the assembly of the sample container 2 on the support tube 34 can be performed, as described in EP 1 711 412 B1. As the annular skirt 15 together with the flange 13 form a cap-like component on the sample container 2, in principle the joining process of the sample containers 2 to the support tube 34 can be performed in an equivalent manner, but adjusted to the components available.

The support tube 34 thereby corresponds with the collection container, as described in EP-B1. In contrast to this in the present invention no sealing device is provided directly inside the annular skirt 15. During the joining process by means of the cap-like annular skirt 15 with its open face end facing towards the support tube 34 the open first end section 35 of the support tube 34 is gripped over.

By providing the two thread arrangements 18, 39 with their interacting threads between the annular skirt 15 and the support tube 34 the assembly can be performed by a relative rotational or pivotal movement about the common longitudinal axis 8. Furthermore, at the same time also a plurality of sample containers 2 can be moved with the support tubes 34 to be joined to form the collection assemblies 1 into a common mounting device, which is not shown here in detail however.

For the joining processes one of the components being assembled is supported rotatably about its longitudinal axis 8 on a pressure bearing of the mounting device, wherein by means of the mounting device on at least one of the components being assembled a pressure force (F) is exerted directed in the direction of the longitudinal axis 8. In this case by means of the cooperating threads of the thread arrangements 18, 39 the pressing force (F) for generating the relative movement is converted into the relative rotational or pivot movement about the common longitudinal axis 8. During the relative rotational or pivotal movement the threads of the thread arrangement 18, 39 can be in engagement with one another over the whole length of the screwing-in path until a fully screwed-on position is reached. This screwing on movement can be ended by lining up the end face of the open first end section 35 of the support tube 34 on the flange 14.

Independently of this however, it would also be possible to have just a plug connection without providing the two thread arrangements 18 or 39.

After performing the centrifugal process and successfully separating the blood into its lighter and heavier components for example the lighter component arranged adjacent to the open end 4 can be removed from the collecting space 12. This can either be performed in that the closure device 3 is removed from the open end 4 of the sample container 2 or the penetrable septum 26 is removed by a removal device not shown in more detail from the collecting space 12. This can be performed for example by a suctioning processor the like.

Figure 5:
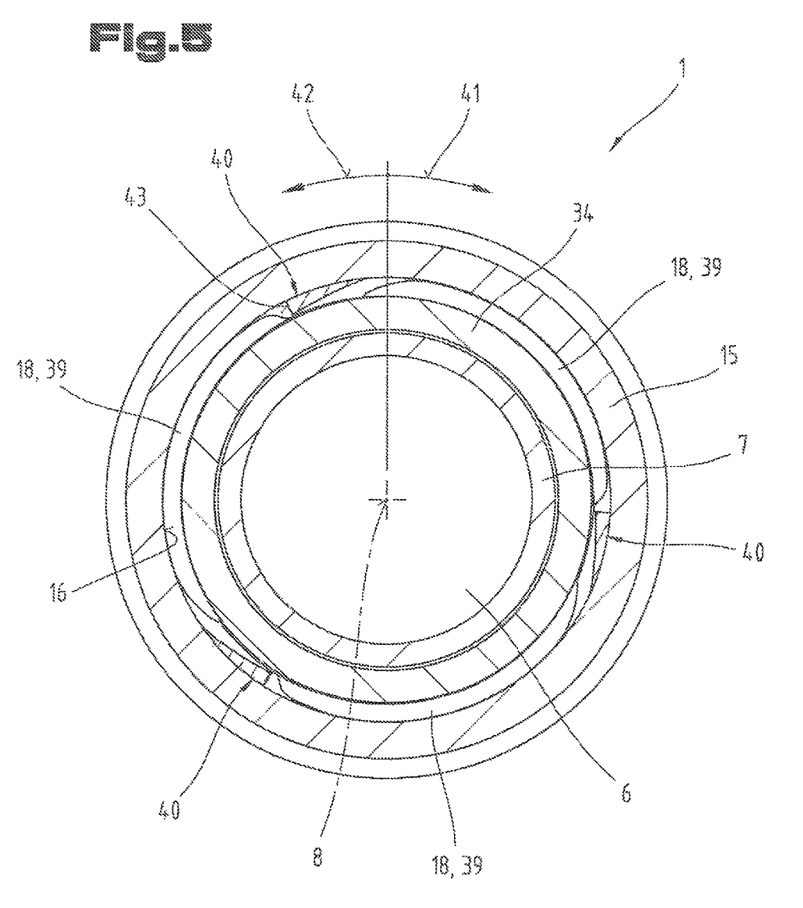
FIG. 5 shows the sample container inserted into a support tube according to FIG. 1 to 4, with an additional anti-rotation device, in plan view in cross-section.

FIG. 5 shows a further and possibly independent embodiment of the collection assembly 1 with the sample container 2 inserted into the support tube 34, in particular connected therewith via the thread arrangements 18, 39 in plan view in cross section, wherein for the same parts the same reference numerals or component names have been used as in the preceding FIG. 1 to 4. To avoid unnecessary repetition reference is made to the detailed description in the preceding FIG. 1 to 4.

For some reasons in the following sample analysis or further processing and treatment of the sample contents of the collection assembly 1, it may be necessary to secure the sample container 2 with its annular skirt 15 after insertion and screwing or connecting to the support tube 34 against an unintentional unscrewing or removal. This may be the case, for example if the sample container 2, in particular its side wall 7, is not provided with an information carrier, but the support tube 34 is. If it were possible to remove or separate the sample container 2 from the support tube 34 it may be the case that only the support tube 34 is provided with the corresponding information or the information carrier and the sample contained in the sample container 2 can be no longer be assigned clearly to one patient because of the absence of labelling.

Therefore, it can be advantageous, if between the cap-like annular skirt 15 of the sample container 2 and the support tube 34 an additional anti-rotation device 40 is provided or arranged. Said anti-rotation device 40 can be formed by very different cooperating locking or securing elements, which make it possible to join the sample container 2 to the support tube 34. On providing the two thread arrangements 18, 39 this is performed by a screwing on movement about the longitudinal axis 8, wherein the direction of rotation for the connecting process is indicated by a first arrow 41. An additional arrow 42 however shows the opposite rotational movement which needs to be made more difficult or completely prevented.

In the present example embodiment the anti-rotation device or devices 40 are formed on the annular skirt surface 16 and also projecting in the direction of the longitudinal axis 8. In order to enable an unhindered screwing on process in the direction of the first arrow 41 here a flat, preferably step-less incline is provided.

In order to prevent the unscrewing or removal of the sample container 2 from the support tube 34 in the opposite rotational movement according to arrow 42, the anti-rotation devices 40 has a locking surface 43 or stop surface. The latter is mostly arranged in a plane aligned perpendicular to the unscrewing movement—according to arrow 42—, in order in this way to achieve an engagement and lining up for example on one of the first threads of the thread arrangements 18. In this way the unscrewing can be made more difficult or completely prevented. However, also other arrangements or configurations of the elements forming the anti-rotation device 40 can be selected. When changing the screwing on direction, as generally known in right-hand or left-hand threads, the arrangement and alignment of the anti-rotation device 40 or the elements thereof need to be adjusted to the respectively selected directions of rotation.

The exemplary embodiments show possible embodiment variants of the collection assembly 1, whereby it should be noted at this point that the invention is not restricted to the embodiment variants shown in particular, but rather various different combinations of the individual embodiment variants are also possible and this variability, due to the teaching on technical procedure, lies within the ability of a person skilled in the art in this technical field.

Furthermore, also individual features or combinations of features of the various exemplary embodiments shown and described can represent in themselves independent or inventive solutions.

The problem addressed by the independent solutions according to the invention can be taken from the description.

Figure 1:
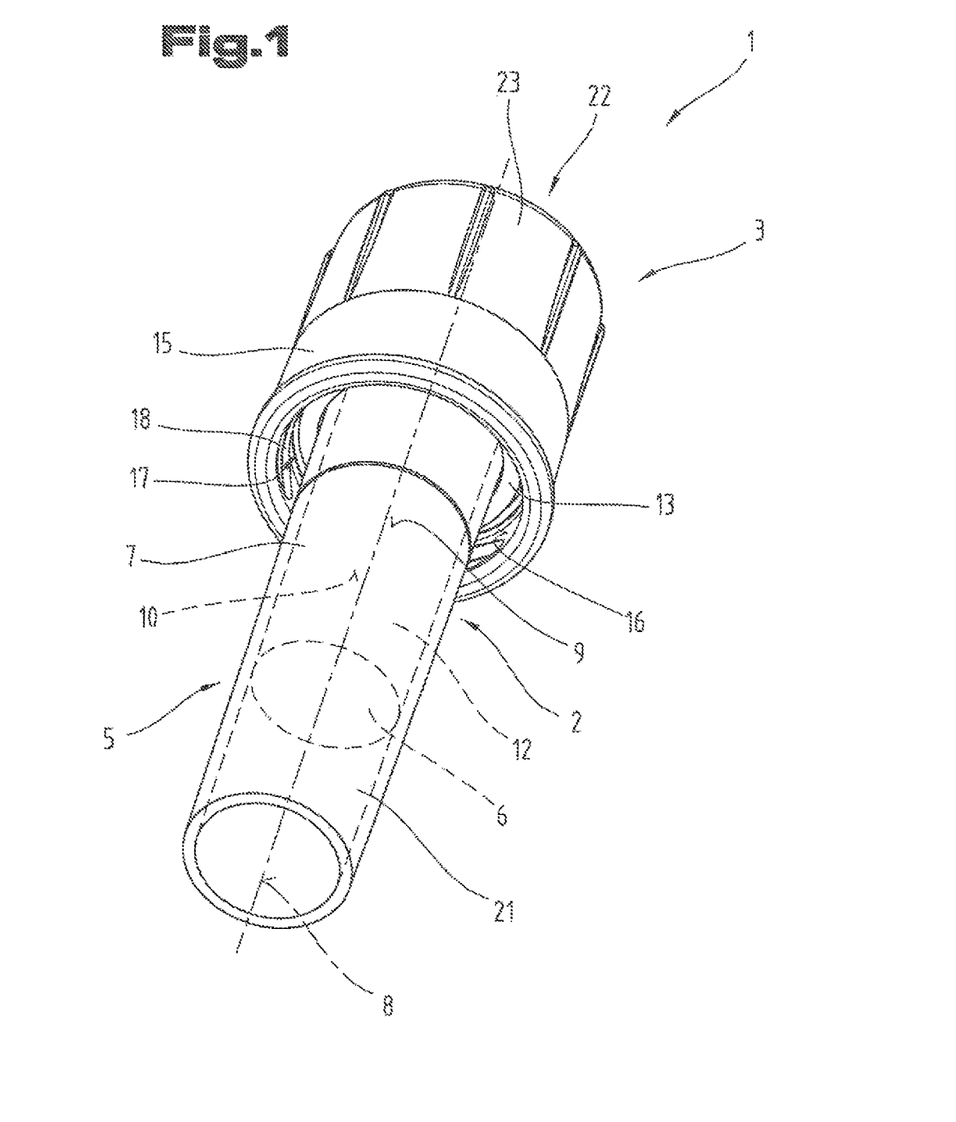
FIG. 1 shows a sample container closed by a closure device, in diagrammatic view.

Mainly the individual embodiments shown in FIGS. 1, 2; 3; 4; 5 can form the subject matter of independent solutions according to the invention. The objectives and solutions according to the invention relating thereto can be taken from the detailed descriptions of these figures.

Finally, as a point of formality, it should be noted that for a better understanding of the structure of the collection assembly 1, the latter and its components have not been represented true to scale in part and/or have been enlarged and/or reduced in size.

List of reference numerals

| | |
|---|---|
| 1 | collection assembly |
| 2 | sample container |
| 3 | closure device |
| 4 | open end |
| 5 | closed end |
| 6 | base |
| 7 | side wall |
| 8 | longitudinal axis |
| 9 | outer surface |
| 10 | inner surface |
| 11 | end face |
| 12 | collecting space |
| 13 | flange |
| 14 | flange end |
| 15 | annular skirt |
| 16 | annular skirt surface |
| 17 | free space |
| 18 | first thread arrangement |
| 19 | receiving edge |
| 20 | receiving edge surface |
| 21 | edge |
| 22 | closure cap |
| 23 | outer cap casing |
| 24 | inner cap casing |
| 25 | end wall |
| 26 | septum |
| 27 | face end |
| 28 | sealing surface |
| 29 | face end |
| 30 | centering arrangement |
| 31 | first centering element |
| 32 | second centering element |
| 33 | holding device |
| 34 | support tube |
| 35 | first end section |
| 36 | support tube base |
| 37 | second end section |
| 38 | outer surface |
| 39 | second thread arrangement |
| 40 | anti-rotation device |
| 41 | arrow |
| 42 | arrow |
| 43 | locking surface |

The invention claimed is:

1. A collection assembly, comprising a sample container, which has an open end, an end closed by a base and a side wall extending between the open end and the closed end with an outer surface and an inner surface, which side wall is delimited in the region of the open end by an end face, and the side wall and the base define a collecting space, and the sample container also comprises on its open end delimited by the end face a flange projecting radially over the side wall and an annular skirt, wherein the annular skirt is arranged on an end of the flange facing away from the side wall, and the annular skirt extends from this flange end in axial direction towards the closed end, wherein the sample container, the flange and the annular skirt form a one-piece component, and between the outer surface of the side wall and an inner annular skirt surface of the annular skirt facing the side wall an approximately tubular free space is formed which is delimited in axial direction in the region of the open end by the flange, wherein the sample container comprises a lip-shaped receiving edge connected to the end face of the side wall, the receiving edge projecting over the end face of the open end in axial direction in the direction facing away from the base, with a closure device, which comprises a closure cap, as well as a pierceable septum held on the closure cap, wherein the closure device in its closed position closes the collecting space of the sample container in the region of its open end, wherein the closure cap comprises an outer cap casing, an inner cap casing arranged inside of and spaced apart from the outer cap casing in radial direction, and an end wall connecting the outer cap casing and the inner cap casing in radial direction, the inner cap casing and the outer cap casing protruding in the same direction from the end wall, wherein in the closed position of the closure device an open face end of the outer cap casing bears between the flange and the annular skirt in a transitional area, wherein the septum is arranged or formed on an open face end of the inner cap casing, the open face end being arranged spaced apart from the end wall of the closure cap, wherein the septum has a radially circumferential sealing surface, the sealing surface in the closed position bearing against the inner surface of the side wall in a sealing manner, wherein a holding device is provided with first and second holding elements working together in the closed position of the closure device, the holding device being arranged between the open face end of the outer cap casing and the transitional area between the flange and the annular skirt, and wherein the flange or the annular skirt has an outer cross-sectional form or an external dimension which corresponds approximately to an outer cross-sectional form or an external dimension of the outer cap casing.

2. The collection assembly as claimed in claim 1, wherein on the inner annular skirt surface a first thread arrangement is arranged or formed.

3. The collection assembly as claimed in claim 1, wherein the receiving edge extends only over a portion of the periphery of the side wall and a receiving edge surface facing the collecting space passes in axial direction in an approximately straight line into the inner surface formed by the side wall.

4. The collection assembly as claimed in claim 1, wherein the sample container at its closed end has a tubular edge, which tubular edge projects over the closed end in axial direction in the direction facing away from the open end.

5. The collection assembly as claimed in claim 1, wherein the septum comprises a self-resealing material.

6. The collection assembly as claimed in claim 1, wherein between the open face end of the outer cap casing and the flange or the annular skirt a centering arrangement is provided with first and second centering elements working together in the closed position.

7. The collection assembly as claimed in claim 1, further comprising a support tube having an open first end section and a second end section closed by a support tube base, wherein the sample container is inserted into the support tube and the open first end section of the support tube projects into the tubular free space formed between the outer surface of the side wall and the annular skirt of the sample container.

8. The collection assembly as claimed in claim 7, wherein the support tube is provided on an outer surface of its open first end section with a second thread arrangement.

9. The collection assembly as claimed in claim 7, wherein between the sample container and the support tube at least one anti-rotation device is arranged or formed, and wherein after joining the sample container to the support tube the at least one anti-rotation device prevents the separation of the sample container from the support tube.

10. The collection assembly as claimed in claim 9, wherein the at least one anti-rotational device is arranged or formed between the annular skirt of the sample container and the support tube.

* * * * *